(12) United States Patent
Bouvet et al.

(10) Patent No.: US 7,173,061 B2
(45) Date of Patent: Feb. 6, 2007

(54) COMPOUNDS FOR IMAGING ALZHEIMER'S DISEASE

(75) Inventors: Denis Raymond Christophe Bouvet, Amersham (GB); Harry John Wadsworth, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 3 days.

(21) Appl. No.: 10/499,069

(22) PCT Filed: Dec. 12, 2002

(86) PCT No.: PCT/GB02/05641

§ 371 (c)(1),
(2), (4) Date: Nov. 26, 2004

(87) PCT Pub. No.: WO03/051859

PCT Pub. Date: Jun. 26, 2003

(65) Prior Publication Data

US 2005/0080130 A1    Apr. 14, 2005

(30) Foreign Application Priority Data

Dec. 19, 2001    (GB) ................... 0130305.6

(51) Int. Cl.
*A61K 31/343*    (2006.01)
*C07D 307/80*    (2006.01)
(52) U.S. Cl. .................. 514/469; 514/917; 549/468; 549/469
(58) Field of Classification Search ............. 549/468, 549/469; 514/469, 917
See application file for complete search history.

(56) References Cited

U.S. PATENT DOCUMENTS 3,947,470 A    3/1976 Brenner et al.
4,024,273 A    5/1977 Brenner et al.
5,846,956 A    12/1998 Plaquevent et al.

FOREIGN PATENT DOCUMENTS

WO    95 17382    6/1995

OTHER PUBLICATIONS

Allsop, et.al., Bioorganic & Medicinal Chemistry Letters, Oxford, GB vol. 11, No. 2, Jan. 2001 pp. 255-257.
Twyman, et.al., Tetrahedron Letters, Elsevier Science Publishers, Amsterdam, NL vol. 40, No. 52, Dec. 24, 1999 pp. 9383-9384.
Howlett, David, et.al., Biochemical Journal (1999), 340(1) pp. 283-289.
Ono, et.al., Nuclear Medicine and Biology, 29(2002) 633-642.
Makesh, et.al., Indian Journal of Chemistry, vol. 17B, Apr. 1979 pp. 382-384.
Singh, The Mannich Research School, Pharmaceutical Chemistry Division, Banara Hindu University, Jan. 21, 1967 p. 264.
Thomas, et.al., Jour. Indian Chem. Socl, vol. 45 No. 3, 1968 pp. 265-269.
Shu, Journal of Labelled Compounds and Radiopharmaceuticals (1999), vol. 42(8), pages.
International Search report PCT/GB02/05641 dated Oct. 3, 2003.
GB 0130305.6 Search report dated Jan. 7, 2002.
IPER for PCT/GB02/05641.

*Primary Examiner*—Taofiq Solola
(74) *Attorney, Agent, or Firm*—Li Cai

(57) ABSTRACT

The invention provides compounds of formula (I) or a salt thereof, radiolabelled versions thereof, and their use in the diagnosis or in vivo imaging of Amyloid-associated diseases such as Alzheimer's disease

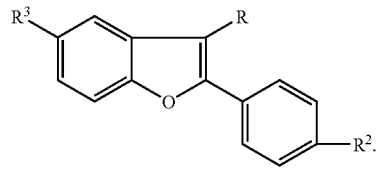

(I)

9 Claims, No Drawings

COMPOUNDS FOR IMAGING ALZHEIMER'S DISEASE

This application is a filing under 35 U.S.C. 371 of international application number PCT/GB02/05641 filed Dec. 12, 2002 which application claims priority to Great Britain application number 0130305.6 filed Dec. 19, 2001

The present invention relates to the field of diagnostic imaging of Alzheimer's disease and provides compounds useful in such diagnostic imaging, as well as methods for their preparation and use.

Alzheimer's disease is the fourth most common cause of death in the western world, after heart disease, cancer and strokes. In the USA there are approximately 4 million people suffering with Alzheimer's disease, at an annual cost of $100 billion. Therefore, the cost per person in the USA is $25,000 per year. There are currently 20 million sufferers of dementia in the world. This is set to double to 40 million by the year 2025 as the number of people aged 65 doubles from 390 million now to 800 million in 2025. Of these 40 million, approximately 56 percent will be suffering from Alzheimer's disease, accounting for 22.2 million.

The in vivo imaging techniques used at present do not in all cases differentiate the diagnosis of Alzheimer's disease from other forms of dementia. The differential diagnosis of patients will become increasingly important as more treatments become available. Imaging agents will also be required to image Alzheimer patients at earlier stages of the disease to allow preventive treatment, and for monitoring disease progression Currently the only definitive test for Alzheimer's disease is examination of the brain at autopsy for the presence of distinctive pathophysiologies. One of the most widely acknowledged of these pathophysiologies is the presence of senile plaques in brain tissue. Senile plaques are deposits of a 40–43 amino acid protein called the β-amyloid protein. They are an early and invariant aspect of the disease and it is thought that the deposition of β-amyloid occurs some time prior to the onset of clinical symptoms.

Amyloid-specific radiotracers have been suggested as potential imaging agents for Alzheimer's disease. Congo Red has been demonstrated to be an effective binder of β-amyloid, but does not cross the blood-brain barrier (BBB) well (Klunk et al 1994 Neurobiology of Aging Vol. 15 pp. 691–698). There is no convincing functional evidence that abnormalities in the BBB reliably exist in Alzheimer's (Kalaria 1992, Cerebrovascular and Brain Metabolism Reviews, Vol 4, p 226). Therefore, an important property of an Alzheimer's in vivo imaging agent is that it crosses the BBB.

U.S. Pat. No. 3,947,470 and U.S. Pat. No. 4,024,273 describe certain benzofuran compounds having coronary vasodilator activity. Howlett et al (Biochem J. (1999), 340, 283–9) describes a series of benzofuran derivatives which are inhibitors of fibril formation in the β-amyloid peptide.

The aim of the present invention is the provision of novel $^{99m}$Tc-labelled agents for in vivo imaging of Alzheimer's disease. To be able to successfully image Alzheimer's disease in vivo, an agent must be capable of crossing the BBB as well as binding to β-amyloid.

Labelling of a compound with $^{99m}$Tc requires that the compound be coupled with a suitable $^{99m}$Tc chelator. It is known in the art that suitable $^{99m}$Tc chelators are relatively bulky molecules, and as such would act to increase the molecular weight of an amyloid-binding agent, in turn decreasing the chances of such an agent crossing the BBB. Similarly, attachment of a suitable $^{99m}$Tc chelator to an amyloid-binding agent would be expected to interfere with the binding properties of the agent. It is therefore surprising that we have found a class of compounds which include chelated $^{99m}$Tc but which may be capable of crossing the BBB and binding with β-amyloid.

In a first aspect, this invention provides a compound of formula (I):

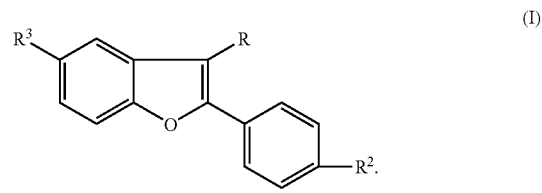

or a salt thereof, wherein either:

(i) R is hydrogen and $R^2$ is the group —OCR$^4$R$^5$[B]-[A] wherein $R^4$ and $R^5$ are independently selected from hydrogen and $C_{1-6}$ alkyl, [A] is a chelate, and [B] is a linking group and is preferably —C(O)NR$^6$— wherein $R^6$ is hydrogen or $C_{1-6}$ alkyl;

or (ii) R is the group

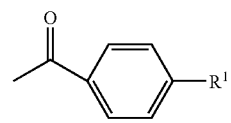

and one of $R^1$ and $R^2$ is the group —OCR$^4$R$^5$[B]-[A] as defined above; and the other is the group —(O)$_n$—C$_{1-6}$ alkyl-NR$^7$R$^8$ wherein n is 0 or 1, and $R^7$ and $R^8$ are independently selected from hydrogen and $C_{1-6}$ alkyl; and $R^3$ is halo, preferably chloro.

In one aspect of the invention, the group R in the compound of formula (I) is hydrogen, therefore there is provided a compound of formula (Ia):

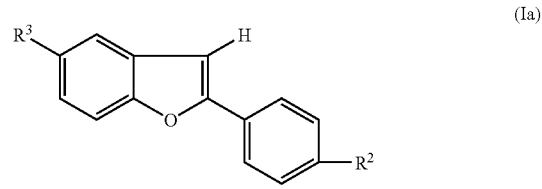

or a salt thereof, wherein $R^2$ is the group —OCR$^4$R$^5$[B]-[A] wherein $R^4$ and $R^5$ are independently selected from hydrogen and $C_{1-6}$ alkyl, [A] is a chelate, and [B] is a linking group and is preferably —C(O)NR$^6$— wherein $R^6$ is hydrogen or $C_{1-6}$ alkyl;

and $R^3$ is halo, preferably chloro.

In a further aspect of the invention, there is provided a compound of formula (Ib):

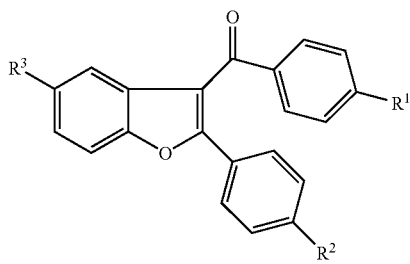

(Ib)

or a salt thereof, wherein:

one of $R^1$ and $R^2$ is the group —$OCR^4R^5$[B]-[A] as for formula (I); and the other is the group —$(O)_n$—$C_{1-6}$ alkyl-$NR^7R^8$ as defined for formula (I); and $R^3$ is halo, preferably chloro.

Preferred compounds of formula (I) include those of formula (Ic):

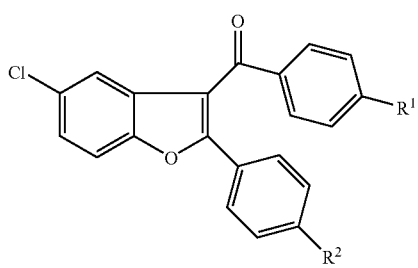

(Ic)

or a salt thereof, wherein:

one of $R^1$ and $R^2$ is —$OCH_2C(O)NH$-[A] wherein [A] is a chelate;

the other is —$O$—$(CH_2)_{2,3}$—$NR^7R^8$ wherein $R^7$ and $R^8$ are independently selected from hydrogen and $C_{1-6}$ alkyl.

Compounds of formula (I) which are of particular interest, include those described in Examples 1(vii), 2(vii), and 8(iii), especially when Pn216 conjugated.

The term "chelate" is defined in the present invention as being a tetradentate metal complexing agent, preferably suitable for complexing technetium. Technetium chelates are discussed in section B of "Technetium: chemistry and radiopharmaceutical applications", Klaus Schwochau, 2000, pp. 373–423, published by Wiley-Vch Verlag GmbH. Suitable chelates of the invention may be selected from:

(i) diaminedioximes of formula (A):

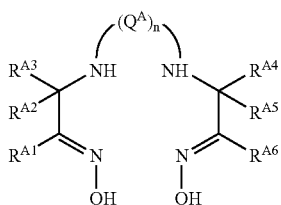

(A)

where $R^{A1}$—$R^{A6}$ are each independently selected from hydrogen, $C_{1-6}$ alkyl, arylalkyl, alkoxyalkyl, hydroxyalkyl, haloalkyl or aminoalkyl;

and -$(Q^A)_n$- is a bridging group wherein n is 3, 4 or 5 and each $Q^A$ is independently selected from —$O$—, —$NR$— and —$CR_2$— where R is hydrogen, $C_{1-6}$ alkyl, arylalkyl, alkoxyalkyl, hydroxyalkyl, fluoroalkyl or aminoalkyl provided that there is a maximum of one $Q_A$ group which is selected from —$O$— or —$NR$—.

(ii) Macrocyclic $N_4$ ligands of formula (B):

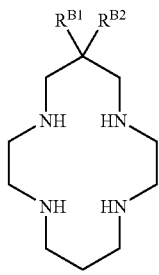

(B)

where $R^{B1}$ and $R^{B2}$ are independently selected from hydrogen, $C_{1-6}$ alkyl, arylalkyl optionally substituted by aminoalkyl, alkoxyalkyl, hydroxyalkyl, haloalkyl or aminoalkyl.

(iii) Diaminediphenols of formula (C):

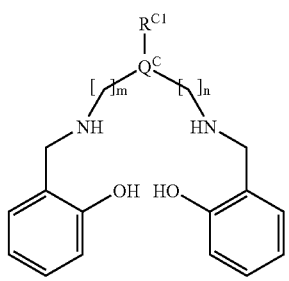

(C)

where $Q^C$ is either $C(R^{C2})$ or N;

$R^{C1}$ and $R^{C2}$ are independently selected from hydrogen, $C_{1-10}$ alkyl, arylalkyl, alkoxyalkyl, hydroxyalkyl, haloalkyl or aminoalkyl, and;

m is equal to n and both are integers suitably selected from 1, 2, 3, and 4.

(iv) $N_2S_2$ ligands of formula (D):

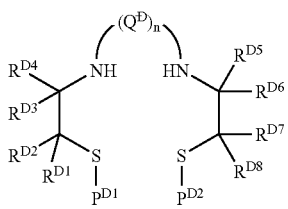

(D)

where $P^{D1}$ and $P^{D2}$ are hydrogen or protecting groups such as benzoyl, acetyl or ethoxyethyl which may be cleaved before or during the labelling process, and;

$R^{D1}$ to $R^{D8}$ are independently selected from hydrogen, $C_{1-10}$ alkyl, arylalkyl, alkoxyalkyl, hydroxyalkyl, haloalkyl or aminoalkyl, and;

one or more of the pairs $R^{D1}/R^{D2}$, $R^{D3}/R^{D4}$, $R^{D5}/R^{D6}$, $R^{D7}/R^{D8}$ may, together with the carbon to which they are attached, represent a C=O group, and $-(Q^D)_n-$ is a bridging group wherein n is 2, 3, 4, or 5 and each $Q^D$ is independently selected from —O—, —NR—, and —CR$_2$— wherein R is hydrogen, $C_{1-6}$ alkyl, arylalkyl, alkoxyalkyl, hydroxyalkyl, haloalkyl, or aminoalkyl, provided that there is a maximum of one $Q^D$ group which is selected from —O— or —NR—.

(v) Hydrazino nicotinamide ligands of formula (E):

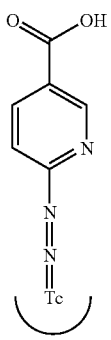

(E)

wherein technetium is co-ordinated in conjunction with a co-ligand selected from formulae (Ei) to (Ev):

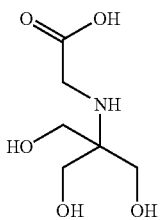

(Ei)

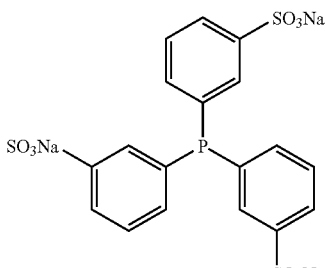

(Eii)

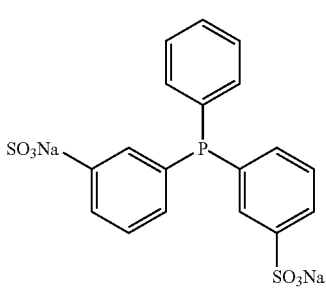

(Eiii)

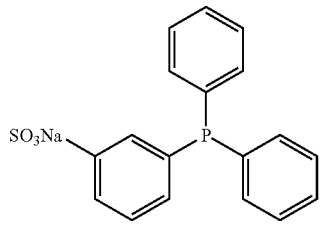

(Eiv)

(Ev)

wherein $R^{E1}$ is selected from hydrogen, benzyl, and $C_{1-6}$ alkyl (suitably methyl) and $R^{E2}$ is selected from hydrogen and —CH$_2$COOH.

Preferred diaminedioximes of formula (A) have $R^{41}$ to $R^{46}$ independently selected from $C_{1-3}$ alkyl, alkylaryl alkoxyalkyl, hydroxyalkyl, fluoroalkyl or aminoalkyl. In the most preferred diaminedioximes, $R^{41}$ to $R^{46}$ are all CH$_3$. One preferred chelating agent of the present invention is a diaminedioxime of formula (A) where $R^{41}$ to $R^{46}$ are all CH$_3$ and $(Q^4)_n$ is —NH(CH$_2$)$_2$N(CH$_2$CH$_2$NH$_2$)(CH$_2$)$_2$NH—. Another preferred chelating agent of the present invention is a diaminedioxime of formula (A) where $R^{41}$ to $R^{46}$ are all CH$_3$ and $(Q^4)_n$ is —CH$_2$C(CH$_3$)(CH$_2$NH$_2$)CH$_2$—. Amyloid binding agents of the invention may be suitably linked to the chelate at any functional residue. Amyloid binding agents of the invention are preferably linked via a functionality in $(Q^4)_n$, and most preferably via an amine group in $(Q^4)_n$ to form the [B] linker group —C(O)NR$^6$—.

Preferred macrocyclic N$_4$ ligands of formula (B) have $R^{B1}$ as H and $R^{B2}$ as aminoalkyl arylalkyl (suitably aminomethyl benzyl, most suitably 4-aminomethyl benzyl). Amyloid binding agents of the invention may be attached to the chelate via any functional group, but preferably via a functional group of $R^{B1}$ or $R^{B2}$. Amyloid binding agents of the invention are most preferably attached to the chelate via a terminal NH$_2$ of $R^{B2}$ to form the [B] linker group —C(O)NR$^6$—.

Preferred diaminediphenols of formula (C) have $Q^C$ as $C(R^{C2})$ and one of $R^{C1}$ and $R^{C2}$ aminoalkyl and the other hydrogen or $C_{1-6}$ alkyl. In a most preferred embodiment, $Q^C$ is $C(R^{C2})$, $R^{C1}$ is CH$_3$ and $R^{C2}$ is CH$_2$NH$_2$. Amyloid binding agents of the invention are suitably attached to any functional residue of the chelate, but preferably to either $R^{C1}$ or $R^{C2}$. Amyloid binding agents of the invention are most preferably attached via a terminal NH$_2$ group of $R^{C2}$ to form the [B] linker group —C(O)NR$^6$—.

In preferred N$_2$S$_2$ ligands of formula (D), $R^{D1}$, $R^{D2}$ and $R^{D7}$ are hydrogen and the pairs $R^{D3}/R^{D4}$ and $R^{D5}/R^{D6}$, together with the carbons to which they are attached are C=O, and $R^{D8}$ is aminoalkyl. In a most preferred N$_2$S$_2$ ligand of the invention, $R^{D1}$, $R^{D2}$, $R^{D7}$, and $R^{D8}$ are methyl, $R^{D3}$, $R^{D4}$ $R^{D5}$, $R^{D6}$ are hydrogen, and $(Q^D)_n$ is —CH$_2$CH(CH$_2$NH$_2$)— or —CH$_2$C(CH$_3$)(CH$_2$NH$_2$)CH$_2$—. Amyloid binding agents of the invention may be suitably attached to any functional group on the chelate, but preferably to a functional group at $Q^D$, and most preferably to a terminal NH$_2$ at $Q^D$ to form the [B] linker group —C(O)NR$^6$—.

Synthesis of these chelate compounds is well known in the art. Diaminedioxime ligands of formula (A) are prepared by the methods described by Jurisson et al (Inorg. Chem. 1986, Vol. 25, pp. 543–549). Macrocyclic N$_4$ ligands of formula (B) are prepared by the methods of (Int. J. Nuc. Med. Biol., 1984, Vol. 2(2), pp. 113–119). Diaminediphenol ligands of formula (C) may be synthesised according to the methods described by Pillai et al (Nucl. Med. Biol. 1993, Vol. 20(2), pp. 211–216). N$_2$S$_2$ ligands of formula (D) are synthesised by the methods of Sun et al (J. Med. Chem. 1996, Vol. 39, pp. 458–470). Hydrazino nicotinamide ligands of formula (E) are synthesised according to the methods described in U.S. Pat. No. 5,206,370.

A "salt" of a compound of formula (I) is defined as ionic versions of the compounds of formula (I) formed by replacing one or more of the hydrogen ions of an acid with another positive ion such as an alkali metal (suitably Na$^+$ or K$^+$).

"Alkyl" used either alone or as part of another group (such as arylalkyl, hydroxyalkyl) is defined herein as any straight or branched C$_n$H$_{2n+1}$ group, wherein unless otherwise specified n is 1 to 10 and preferably n is 1 to 6.

The term "halo" means a group selected from fluoro, chloro, bromo and iodo.

As stated above, for in vivo imaging purposes, the compounds of the invention are radiolabelled. Therefore, in a further aspect of the present invention is provided a radiolabelled version of the compound of the invention. A radiolabelled compound of the invention is suitably labelled with γ-emitting radioisotopes useful for single photon emission computed tomography (SPECT) imaging. The most preferred imaging moieties are γ-emitting radiometals, in particular $^{99m}$Tc. In the case of $^{99m}$Tc, labelling is accomplished by the complexation of $^{99m}$Tc by the chelate portion of the compound of the invention. The use of $^{99m}$Tc in radiopharmaceutical applications is discussed in section B of "Technetium: chemistry and radiopharmaceutical applications", Klaus Schwochau, 2000, pp. 373–423, published by Wiley-Vch Verlag GmbH.

A compound of formula (I) may be used for the manufacture of a medicament for the in vivo imaging or diagnosis of an amyloid-associated disease. Such a medicament is preferably radiolabelled and most preferably $^{99m}$Tc labelled. Where the medicament is $^{99m}$Tc labelled, sterile $^{99m}$Tc-pertechnetate (TcO$_4^-$) is obtained from a $^{99m}$Tc radioisotope generator by elution with sterile saline. $^{99m}$TcO$_4^-$ produced from a generator is relatively unreactive, and must be reduced to a lower oxidation state before use as a radiopharmaceutical. The most commonly used reducing agent is stannous chloride. Radiolabelling is carried in a mixture comprising a compound of the invention, TcO$_4^-$, and a suitable reducing agent by methods known to those skilled in the art (see section B of "Technetium: chemistry and radiopharmaceutical applications", Klaus Schwochau, 2000, pp. 373–423, published by Wiley-Vch Verlag GmbH).

Accordingly, a further aspect of the present invention is the use of a Tc radiolabelled compound of the invention for therapeutic and diagnostic methods, for example, in vivo imaging and diagnosis of amyloid-associated diseases. "Amyloid-associated diseases" include Alzheimer's disease, familial Alzheimer's disease, type II diabetes, Down's syndrome, homozygotes for the apolipoprotein E4 allele, rheumatoid arthritis, systemic amyloidosis (primary and secondary), and haemorrhagic stroke. Preferably, the compounds of the invention may be used to image Alzheimer's disease.

In the alternative, there is provided a method for in vivo imaging and diagnosis of amyloid-associated disease in a subject comprising administration of a radiolabelled compound of the invention. "Amyloid-associated" include Alzheimer's disease, familial Alzheimer's disease, type II diabetes, Down's syndrome, homozygotes for the apolipoprotein E4 allele, rheumatoid arthritis, systemic amyloidosis (primary and secondary), and haemorrhagic stroke. The method is especially preferred for in vivo imaging and diagnosis of Alzheimer's disease.

A radiolabelled compound according to the invention is preferably administered in a radiopharmaceutical formulation comprising the compound of the invention. A "radiopharmaceutical formulation" is defined in the present invention as a formulation comprising a radiolabelled compound of the invention preferably a Tc labelled compound in a form suitable for administration to humans. Administration is preferably carried out by injection of the formulation as an aqueous solution. Such a formulation may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid) or bulking agents for lyophilisation (such as sodium chloride or mannitol). The radiopharmaceutical formulation is administered in an amount which gives a reliable image, for example for a Tc-labelled compound, in an amount of 0.1 to 50 mCi in about 0.5 to 5.0 ml at the time of administration.

Conveniently, in a further embodiment of the invention, a kit for the preparation of $^{99m}$Tc-labelled compounds for imaging and diagnosis of amyloid-associated disease is provided. A "kit" as defined by the present invention is an embodiment of the invention designed to give sterile, pyrogen-free radiopharmaceutical products suitable for human administration, e.g. via injection into the bloodstream. When the radiometal is $^{99m}$Tc, the kit comprises a vial containing the compound-chelate conjugate of the invention together with a pharmaceutically acceptable reducing agent such as sodium dithionite, sodium bisulphite, ascorbic acid, formamidine sulphinic acid, stannous ion, Fe(II) or Cu(I), preferably a stannous salt such as stannous chloride or stannous tartrate. In use, a source of $^{99m}$Tc is added to the vial to produce the radiolabelled compound.

Compounds of formula (I) in which R is the group

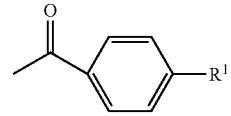

may be prepared from the corresponding compound of formula (II)

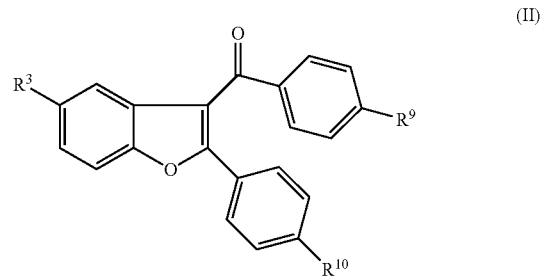

(II)

or a protected derivative thereof, wherein one of R$^9$ and R$^{10}$ is —OCR$^4$R$^5$C(O)OH wherein R$^4$ and R$^5$ are as defined for the compound of formula (I);

the other is —(O)$_n$—C$_{1-6}$ alkyl-NR$^7$R$^8$ wherein n, R$^7$, and R$^8$ are as defined for the compound of formula (I); and R$^3$ is as defined for the compound of formula (I);
by coupling with a chelate of formula

H$_2$N-[A]

wherein [A] is as defined for the compound of formula (I).

Compounds of formula (I) in which R$^6$ is C$_{1-6}$ alkyl may be prepared by alkylation of the corresponding compound of formula (I) in which R$^6$ is hydrogen.

This coupling reaction may be performed using standard methods of amide bond formation. For example, the reaction may be performed in an aprotic solvent, such as N,N-dimethyl formamide, in the presence of an organic base such as N-methylmorpholine (NMM) and 2-(1H-benzotriazole-1-yl)-1,1,3,3-tetramethyluronium tetrafluoroborate (TBTU), at a non-extreme temperature such as 10° to 40° C., preferably at ambient temperature.

Compounds of formula (II) are useful intermediates in the preparation of compounds of formula (I) and therefore represent a further aspect of the present invention.

Compounds of formula (II) may conveniently be prepared by hydrolysis of the corresponding ester, suitably a C$_{1-6}$ alkyl ester, preferably the methyl ester. The hydrolysis may be performed using conventional methods, suitably alkali or acid hydrolysis, for example using aqueous sodium hydroxide.

Esterified compounds of formula (II) may be prepared from the corresponding compound of formula (III)

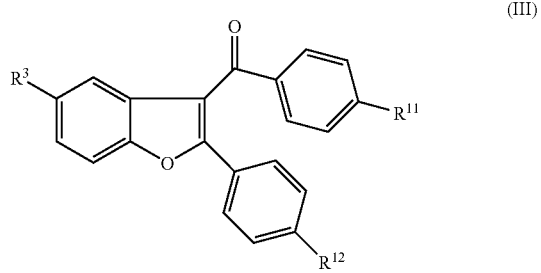

(III)

wherein one of R$^{11}$ and R$^{12}$ is hydroxy and the other is —(O)$_n$—C$_{1-6}$ alkyl-NR$^7$R$^8$ wherein n, R$^7$, and R$^8$ are as defined for the desired compound of formula (II);
and R$^3$ is as defined for the compound of formula (II);
by reaction with the bromoacetate of formula BrCR$_4$R$^5$C(O)OCH$_3$ wherein R$^4$ and R$^5$ are as defined in the compound of formula (II) and are preferably both hydrogen.

Compounds of formula (III) may be prepared by methods analogous to those described in the literature (for example in Howleft et al, see above) or using the methods described in the examples below.

Compounds of formula (I) in which R is hydrogen, may be prepared from the corresponding compound of formula (IV):

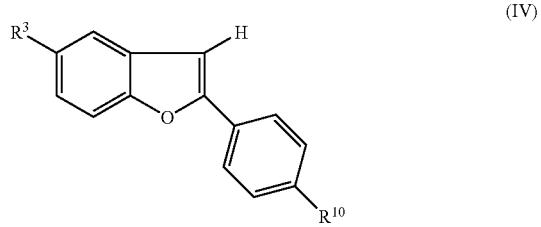

(IV)

or a protected derivative thereof, wherein R$^{10}$ is —OCR$^4$R$^5$C(O)OH as defined for the compound of formula (II); and
R$^3$ is as defined for the compound of formula (I);
by coupling with a chelate of formula

H$_2$N-[A]

wherein [A] is as defined for the compound of formula (I).

Coupling of a compound of formula (IV) with the chelate may be achieved as described above for coupling a compound of formula (II) with a chelate.

Compounds of formula (IV) may be prepared by methods analogous to those described above for preparation of compounds of formula (II) and as exemplified below.

The invention may be illustrated by the following non-limiting examples.

EXAMPLES

Intermediate 1A

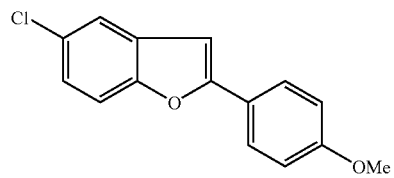

Step(i)

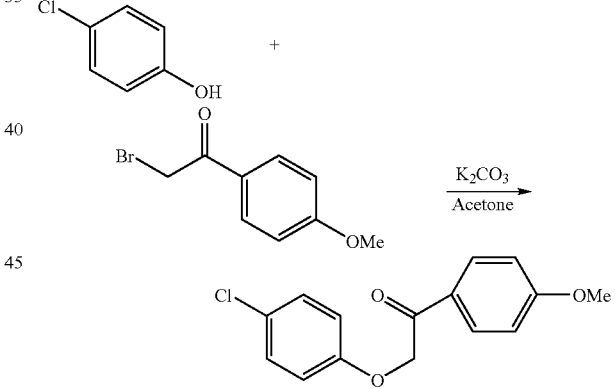

To a solution of 4-chlorophenol (Aldrich) (2.134 g, 16.6 mmol, 1 eq) and 4-methoxy bromoacetophenone (Aldrich) (4.183 g, 18.26 mmol, 1.1 eq) in acetone (50 mL) was added potassium carbonate (3.516 g, 1.53 eq, 25.48 mmol). The mixture was stirred and heated at reflux temperature for 5 hours. The reaction was then allowed to cool to room temperature, and filtered. The filtrate was evaporated to dryness, then dissolved in ethyl acetate (50 mL). The organic layer was then washed sequentially with 2M (NaOH)-twice, water, and saturated NaCl solution. The organic layer was then dried (Na$_2$SO$_4$), filtered and evaporated to dryness to afford a yellow solid. This was crystallised using ethyl acetate (EtOAc)/Petrol to afford the desired product as an off white crystal.

$^1$H NMR (CDCl$_3$) δH ppm 3.86 (s, 3H, OCH$_3$), 5.18 (s, 2H, CH$_2$), 6.82 (d, 2H, aromatic), 6.96 (d, 2H, aromatic), 7.21 (d, 2H, aromatic), 7.96 (d, 2H, aromatic)

Step(ii)

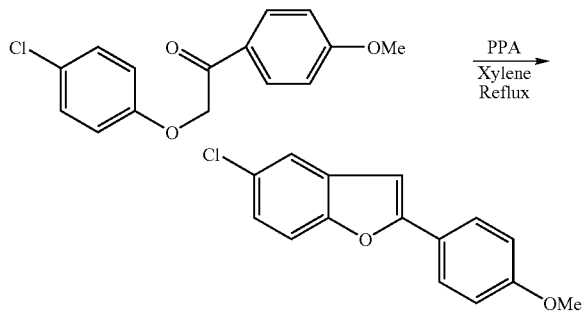

The compound of step (i) (3.244 g, 11.72 mmol)(30) was added to a mixture of polyphosphoric acid (50 g) and xylene (50 mL), and stirred using an overhead stirrer. The resultant mixture was heated at 140 C until completion (monitoring by thin-layer chromatography (TLC)). The reaction mixture was allowed to cool to room temperature (RT) and ethyl acetate (100 mL) was added. The upper organic layer was decanted off. The polyphosphoric acid was treated with water (100 mL) and eliminated from the flask. A further 200 mL water was added, and the aqueous phase was extracted with 3×100 mL EtOAc. The combined organic layer were then washed with brine (100 mL), dried ($Na_2SO_4$), filtered and evaporated to afford a crude solid. This was purified by recrystallisation using ethyl acetate.

$^1$H NMR ($CDCl_3$) δH ppm 3.84 (s, 3H, $OCH_3$), 6.80 (s, 1H, aromatic), 6.95 (d, 2H, aromatic), 7.18 (d, 1H, aromatic), 7.39 (d, 2H, aromatic), 7.49 (d, 1H, aromatic), 7.77 (d, 2H, aromatic).

Intermediate 1

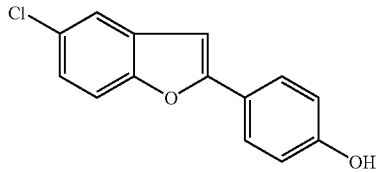

A solution of Intermediate 1A (100 mg, 0.38 mmol)(21) under nitrogen, in dichloromethane (DCM)(7 mL) was cooled in an ice bath. Boron tribromide solution (1M in DCM, 3.8 mL, 3.8 mmol, 10 eq) was added slowly. The dark brown reaction mixture was stirred under $N_2$, and allowed to warm slowly to room temperature. After 4 hours, TLC indicated that reaction was complete (eluant: 5:1 petrol ether:ethyl acetate). The reaction was quenched by addition of 20 mL 10% HCl solution, and was diluted with DCM.

The organic layer was separated off, and the aqueous phase was extracted with ethyl acetate. The organic layers were dried ($Na_2SO_4$), filtered and evaporated to dryness to afford a dirty brown/black solid. This was purified by flash column chromatography (eluent 5:1 petrol:ethyl acetate) to afford a light brown solid.

$^1$H NMR ($CDCl_3$) δH ppm 6.79 (s, 1H, aromatic), 6.87 (d, 2H, aromatic), 7.18 (d, 1H, aromatic), 7.37 (d, 1H, aromatic), 7.49 (d, 1H, aromatic), 7.73 (d, 2H, aromatic).

Intermediate 2 diethyl(3-chloropropyl)amine

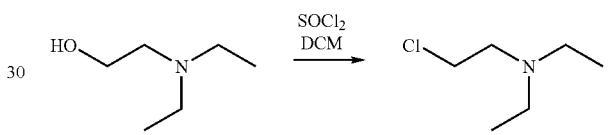

A solution of 3-diethylamino-1-propanol (Aldrich) (10 g, 76 mmol) in DCM was stirred at 0° C. A solution of thionyl chloride (DCM 30 mL) was then added drop-wise such that the reaction temperature remained at 0° C. Once addition is complete, the reaction was refluxed for one hour. The reaction was allowed to cool and the excess DCM and thionyl chloride were removed under vacuum. The residue was basified (pH8–9) using 2N NaOH and the aqueous mixture extracted with DCM (3×100 mL). The organic extracts were combined, dried ($MgSO_4$) and evaporated to give a brown oil. The oil was distilled (160°–165° C.) to give the product as a clear oil (4.2 g 36.9%).

$^1$H NMR ($CDCl_3$) δH ppm 1.02 (6H, 2×$CH_3$), 1.89 (2H, $CH_2$), 2.53 (6H, 3×$CH_2$), 3.59 (2H, $CH_2$)

m/z 150/151 M+H

Intermediate 3 diethyl-chloroethylamine

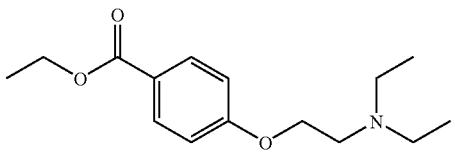

A solution of 2-diethylaminoethanol (Lancaster) (10 g, 85 mmol) in DCM was stirred at 0° C. A solution of thionyl chloride (30 mL DCM) was added such that the temperature of the reaction remained at 0° C. Once addition is complete, the reaction is refluxed for one hour. The reaction is allowed to cool and the excess DCM and thionyl chloride were removed under vacuum. The residue was basified (pH8–9) using 2N NaOH and the aqueous mixture extracted with DCM (3×100 mL). The organic extracts were combined, dried ($MgSO_4$) and evaporated to give a brown oil. The oil was distilled (165°–169° C.) to give the product as a clear oil (6.7 g 58%).

$^1$H NMR ($CDCl_3$) δH ppm 1.02 (6H, 2×$CH_3$), 2.58 (4H, 2×$CH_2$), 2.78 (2H, $CH_2$) 3.52 (2H, $CH_2$)

m/z 136/137 M+H

Example 1

Example 1(i)

ethyl-4-(diethylaminoethyloxy)benzoate

The title compound was prepared by alkylation of ethyl-4-hydroxybenzoate with diethylchloroethylamine using methods analogous to those described in Example 2(i).

¹H NMR (CDCl₃) δH ppm 1.07 (6H, 2×CH₃), 1.38 (3H, CH₃), 2.63 (4H), 2.89 (2H, CH₂), 4.1 (2H, OCH₂)4.35 (2H, OCH₂), 6.91 (2H), 7.97 (2H).

Example 1(ii)

4-(3-diethylaminoethyloxy)benzoic acid

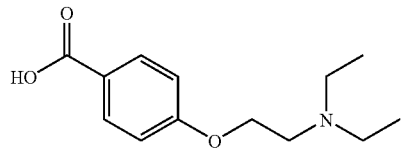

The title compound was prepared from the compound of Example 1(i) using methods analogous to those described in Example 2(ii) to give the expected product 5.2 g, 91% yield.
¹H NMR (d⁶DMSO) δH ppm 1.22 (6H, 2×CH₃), 3.18 (4H), 3.49 (2H, CH₂), 4.46 (2H, OCH₂), 7.05 (2H), 7.89 (2H).

Example 1(iii)

4-(2-diethylaminoethyloxy)benzoyl chloride

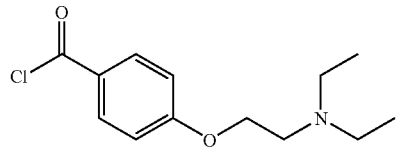

The title compound was prepared from the compound of Example 1(ii) using methods analogous to those in Example 2(iii), to give 5.4 g, 100% yield.
¹H NMR (d⁶DMSO) δH ppm 1.27 (6H, 2×CH₃), 3.17 (4H), 3.49 (2H) 4.47 (2H, OCH₂), 7.07 (2H), 7.9 (2H).

Example 1(iv)

5-chloro-2-(4-methoxyphenyl)-3-[4-(2-diethylaminoethyloxy)benzoyl]benzofuran

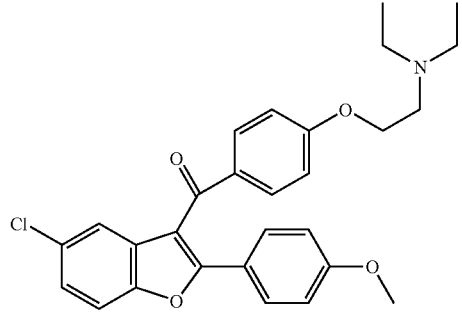

The methods of Example 2(iv) were used to couple Intermediate 1A to the compound of Example 1(iii) to give the expected product (1.21 g, 68%)
¹H NMR (CDCl₃) δH ppm 1.28 (6H, 2×CH₃), 2.99 (4H), 3.22 (2H), 3.81 (3H, CH₃), 4.38 (2H, OCH₂), 6.84, (4H), 7.27 (1H), 7.46 (2H), 7.63 (2H), 7.83 (2H).

Example 1(v)

5-chloro-2-(4-hydroxyphenyl)-3-[4-(3-diethylaminoethyloxy)benzoyl]benzofuran

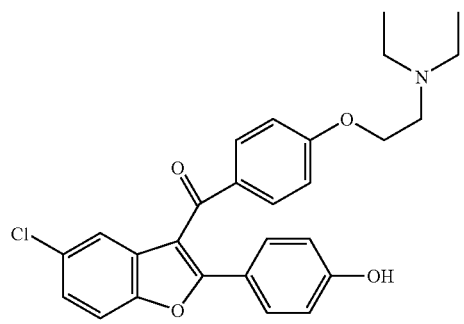

The title compound was prepared from the compound of Example 1(iv) using methods analogous to those described in Example 2(v).
¹H NMR (DMSO) δH ppm 0.91 (6H, 2×CH₃), 2.5 (4H), 2.27 (2H), 4.03 (2H, OCH₂), 6.96 (2H), 6.87 (2H), 7.35 (4H), 7.68 (3H).

Example 1(vi)

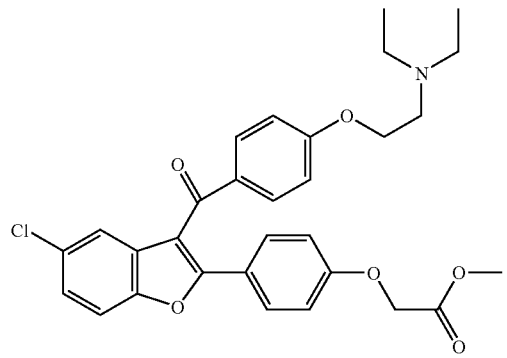

The title compound was prepared from the compound of Example 1(v) using methods analogous to those described in Example 4(iv).
¹H NMR (DMSO) δH ppm 0.91 (6H, 2×CH₃), 2.6 (4H), 2.88 (2H), 3.8 (3H), 4.03 (2H, OCH₂), 4.67 (2H), 6.84 (4H), 7.4 (1H), 7.49 (2H), 7.61 (2H), 7.84 (2H).

Example 1(vii)

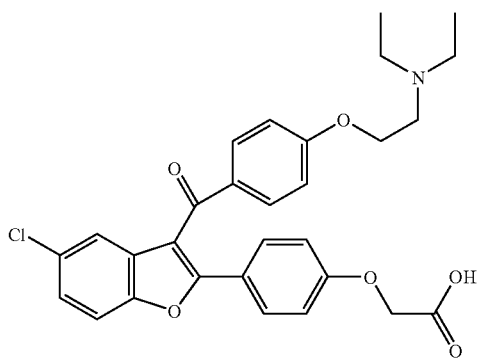

The title product was prepared from the corresponding methyl ester using the following route:

A solution of the compound of Example 1(vi) in methanol was stirred at RT. 2N NaOH (equivalent volume) was added and the reactions were stirred at RT for 2 hours. The reaction was diluted with H$_2$O and acidified to pH4. The aqueous was extracted with DCM (3×) and the organic extracts were combined, dried and evaporated to give the title compound.

$^1$H NMR (CDCl$_3$) δH ppm 1.36 (6H, 2×CH$_3$),3.25 (6H), 4.4 (2H, OCH$_2$), 4.5 (2H), 6.62 (2H), 6.68 (2H), 7.14 (2H), 7.34 (1H), 7.46 (1H), 7.53 (2H), 8.1 (1H).

m/z 522.26/524.49

Example 1(viii)

Coupling to Chelate

The benzofuran of Example 1(vii) (1 eq) and chelate (as a free primary amine)(1 eq) are dissolved in dimethylformamide. TBTU (2-(1H-benzotriazole-1-yl)-1,1,3,3,-tetramethyluroniumtetrafluoroborate) (1.2 eq) and N-methylmorpholine (1.2 eq) are then added. The reaction is stirred at room temperature for 12 hours. The final product is purified by preparative HPLC (PRP column) without any further treatments.

Pn44 Conjugated (from Example 1(vii))

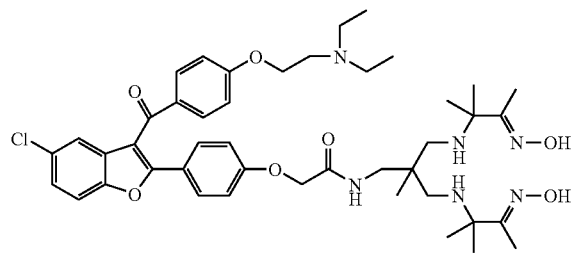

M/S: ES+: m/z 819.3, 410.6; M+H, (M+2)/2

Pn216 Conjugated (from Example 1(vii))

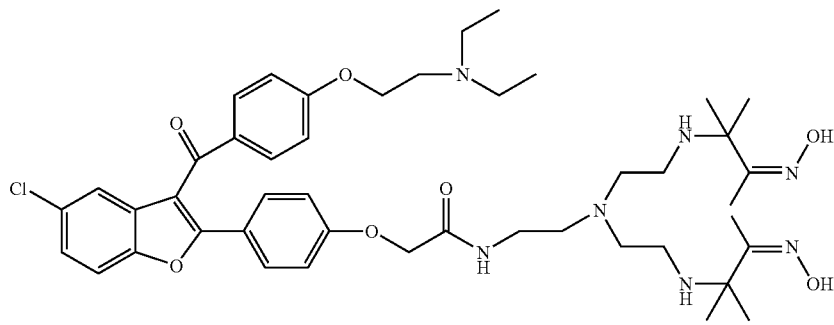

M/S: ES+: m/z 848.2, 425.1; M+H, (M+2)/2 cPn216 Conjugated (from Example 1(vii))

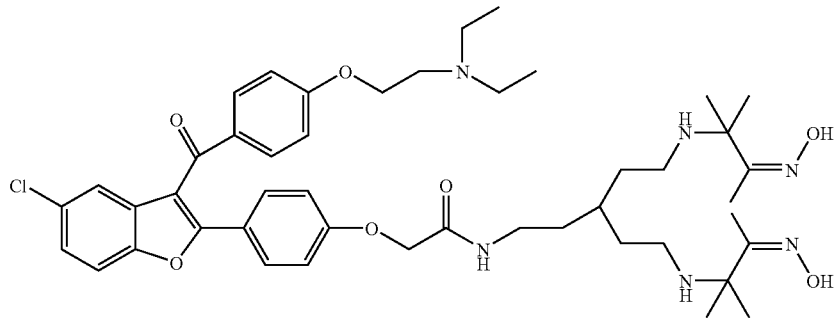

M/S: ES+: m/z 847.3, 424.6; M+H, (M+2)/2

Example 2

Example 2(i)

ethyl-4-diethylaminopropyloxy)benzoate

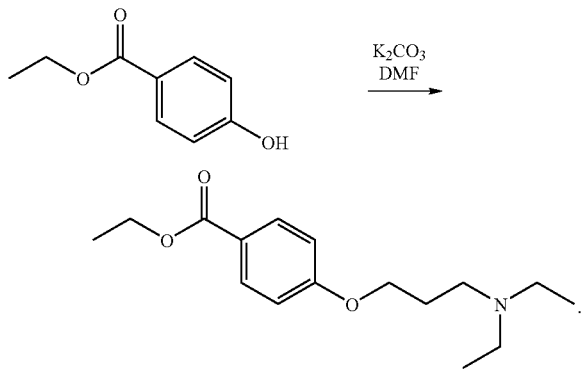

A solution of ethyl-4-hydroxybenzoate (10 g, 6 mmol), Intermediate 2 (10 g, 6.7 mmol) and potassium carbonate (16.6 g, 12 mmol) in DMF was heated at 100° C. for 48 hours. On completion, the reaction was poured onto 200 mL ice-water and the mixture extracted using ethyl acetate (3×100 mL). The organic extracts were combined, dried ($Na_2SO_4$) and evaporated. The residue was purified by flash chromatography to give the title compound 7.6 g, 61% as a pale orange oil.

$^1$H NMR ($CDCl_3$) δH ppm 1.07 (6H, 2×$CH_3$), 1.35 (3H, $CH_3$), 1.92 (2H, $CH_2$), 2.56 (6H), 4.06 (2H, $OCH_2$) 4.35 (2H, $OCH_2$), 6.91 (2H), 7.97 (2H).

Example 2(ii)

4-(3-diethylaminopropyloxy)benzoic acid

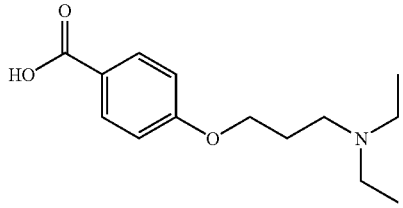

A solution of the compound from Example 2(i) (8 g, 29 mmol) in $H_2O$ (50 mL) was stirred at RT. Conc. HCl was added (50 mL) and the reaction was heated at reflux for 18 hours. The reaction was allowed to cool and evaporated to dryness. The solid was dissolved in hot ethanol and petroleum ether was added to afford the expected product as white platelets, 72 g, 88%.

$^1$H NMR ($d^6$DMSO) δH ppm 1.19 (6H, 2×$CH_3$), 2.17 (2H), 3.12 (6H, $CH_2$), 4.14 (2H, $OCH_2$), 7.02 (2H), 7.88 (2H).

Example 2(iii)

4-(diethylaminopropyloxy)benzoyl chloride

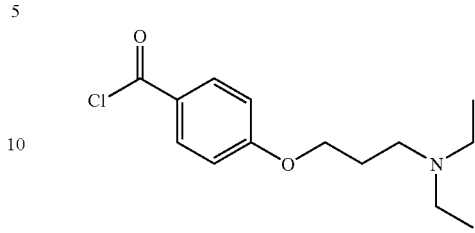

A solution of the compound from Example 2(ii)(6 g, 24 mmol) in DCM was stirred at 0° C. Thionyl chloride was added drop-wise and the reaction was heated at reflux for 24 hrs. The reaction was allowed to cool and the solvents removed under vacuum to afford the expected compound as a pungent crude solid. 5.9 g, 100%. The solid was used without further purification.

$^1$H NMR ($d^6$DMSO) δH ppm 1.19 (6H, 2×$CH_3$), 2.16 (2H), 3.12 (6H) 4.12 (2H, $OCH_2$), 7.03 (2H), 7.89 (2H).

Example 2(iv)

5-chloro-2-(4-methoxyphenyl)-3-[4-(3-diethylaminopropyloxy)benzoyl]benzofuran

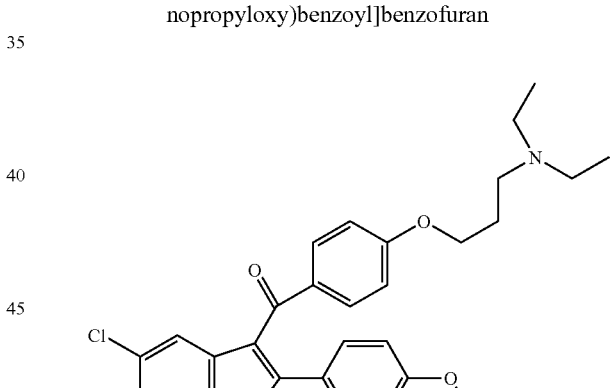

A solution of 5-chloro-2-(4-methoxyphenyl)benzofuran (1 g, 3.9 mmol) in DCM (100 mL) was stirred at 0° C. under nitrogen. The compound of Example 2(iii) (1.68 g, 6.9 mmol) was added followed by the drop-wise addition of tinIV chloride solution (1M DCM, 11.6 mmol). The colour became a deep red and the reaction was stirred at RT. for 3 hrs. The resulting suspension was poured onto ice-water (250 mL) and the organic portion separated. The aqueous layer was extracted with DCM and the organic portions were combined, dried ($Na_2SO_4$) and evaporated. The residue was purified by flash chromatography to give the title compound as a yellow tar (1.34 g, 72%).

$^1$H NMR ($CDCl_3$) δH ppm 1.38 (6H, 2×$CH_3$), 2.36 (2H), 3.12 (4H), 3.81 (3H, $CH_3$), 4.12 (2H, $OCH_2$), 6.83, (4H), 7.29 (1H), 7.46 (2H), 7.65 (2H), 7.82 (2H).

Example 2(v)

5-chloro-3-[4(3-diethylaminopropyloxy)benzoyl]-2-(4-hydroxyphenyl)benzofuran

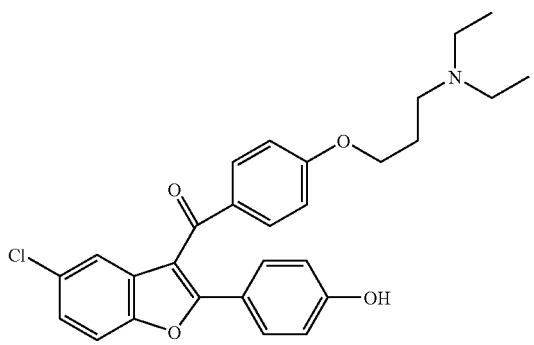

A solution of the compound of Example 2(iv) (4.3 g, 8.7 mmol) in dichloroethane (100 mL) was cooled to 10° C. Aluminium chloride (50 mmol) was added followed by 2-methyl-5-tertbutyl thiophenol (17.4 mmol) and the reaction was heated at 40° C. for 4 hours. Methanol (20 mL) was added followed by H$_2$O (150 mL). The organic phase was separated, concentrated under vacuum and purified by flash chromatography to give the expected compound as a bright yellow oil. 1.9 g, 46% yield.

$^1$H NMR (CDCl$_3$) δH ppm 1.34 (6H, 2×CH$_3$), 2.18 (2H), 3.08 (6H), 4.05 (2H, OCH$_2$), 6.66 (2H), 6.79 (2H), 7.25 (3H), 7.43 (1H), 7.60 (2H), 7.75 (1H).

Example 2(vi)

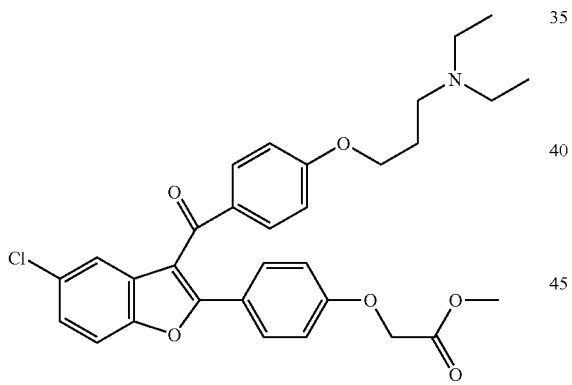

The title compound was prepared from the compound of Example 2(v) using methods analogous to those described in Example 4(iv).

$^1$H NMR (CDCl$_3$) δH ppm 0.18 (6H, 2×CH$_3$), 2.1 (2H), 2.8 (6H), 3.8 (3H) 4.07 (2H), 4.63 (2H, OCH$_2$), 6.84 (4H), 7.26 (2H), 7.45 (1H), 7.64 (2H), 7.83 (2H).

Example 2(vii)

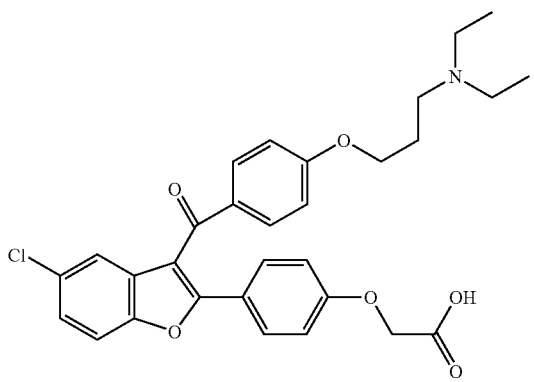

The title compound was prepared using methods analogous to those described in Example 1(vii).

δH ppm 1.12 (6H, 2×CH$_3$), 2.07 (2H), 6.76 (6H), 4.22 (2H, OCH$_2$), 4.5 (2H), 6.85 (2H), 6.94 (2H), 7.5 (3H), 7.65 (1H), 7.76 (2H), 7.82 (1H).

m/z 536.34/538.37

Example 2(viii)

The benzofuran of Example 2(vii) was coupled to various chelates using methods analogous to those described in Example 1(viii).

Pn44 Conjugated (from Example 2(vii))

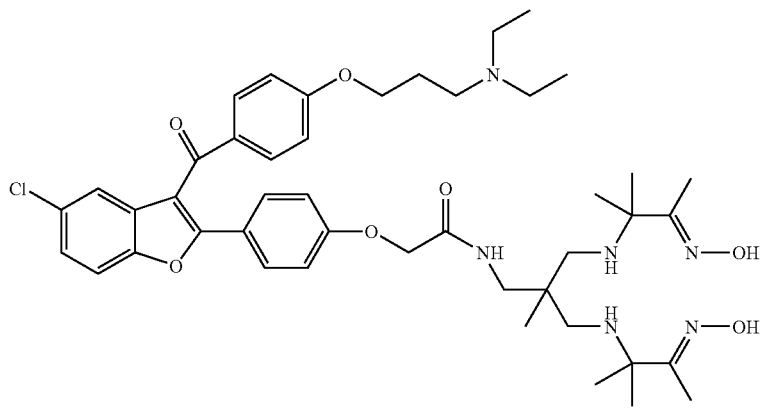

M/S: ES+: m/z 833.3, 417.5, M+H, (M+2)/2

Pn216 Conjugated (from Example 2(vii))

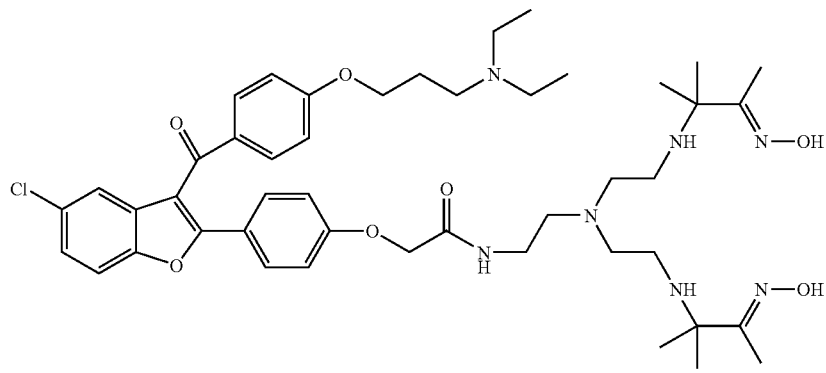

M/S: ES+: m/z 862.3, 432.1, M+H, (M+2)/2 cPn216 Conjugated (from Example 2(vii))

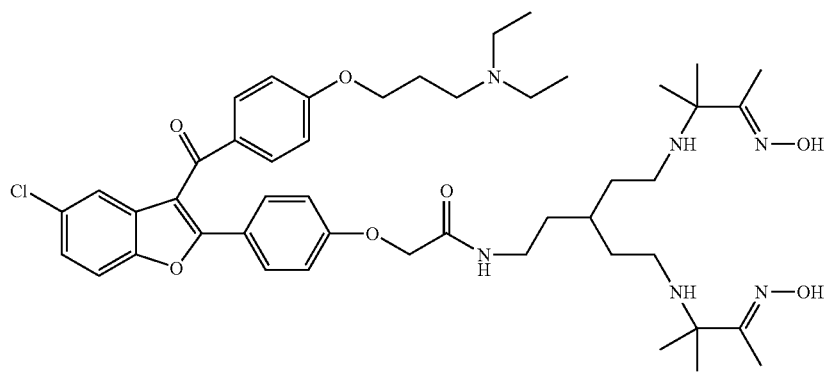

M/S: ES+: m/z 861.3, 431.7, M+H, (M+2)/2

Example 3

Example 3(i)

5-chloro-2-[4(2-diethylaminoethyloxy)phenyl]benzofuran

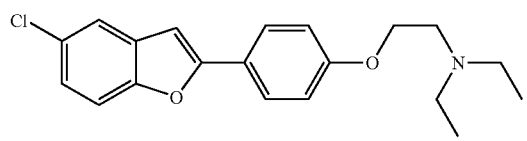

A solution of Intermediate 1 (5 g, 20 mmol) in DMF was stirred at RT. Intermediate 3 (22 mmol) was added followed by potassium carbonate. The reaction was heated to 90° C. for 2 hours. The reaction was allowed to cool and was then poured onto ice-water. The resulting solid was collected by filtration and dried to give the title compound as a white solid 4.5 g, 65.5%).

$^1$H NMR (CDCl$_3$) δH ppm 1.08 (6H, 2×CH$_3$), 2.65 (2H, 2×CH$_2$), 2.91 (4H, 2×CH$_2$), 4.09 (2H, OCH$_2$) 6.8 (1H), 6.97 (2H), 7.18 (1H), 7.38 (1H), 7.49 (1H), 7.76 (2H)

m/z 342/344 M+H

Example 3(ii)

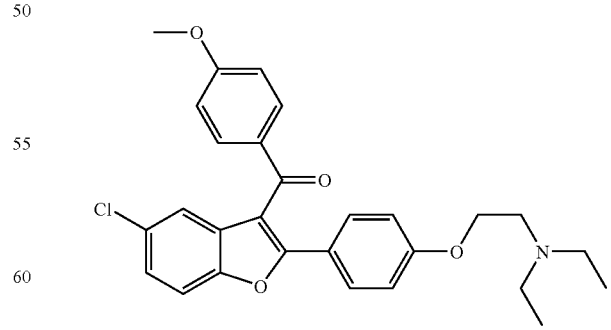

A solution of the compound of Example 3(i) (3.5 g, 10 mmol) and p-anisoylchloride (18 mmol) in dry DCM was stirred at 0° C. under nitrogen. A solution of SnCl$_4$ (1M DCM, 30 mmol) was added drop-wise and stirring was continued for 2 hours at RT. under nitrogen. The reaction mixture was added carefully to 100 mL of ice-water and the aqueous was extracted with ethylacetate (3×100 mL). The organic extracts were combined, dried (Na$_2$SO$_4$) and evaporated to give a bright yellow oil. This was purified by flash chromatography (silica flash) to give the title compound as a white solid. (2.1 g 45%).

$^1$H NMR (CDCl$_3$) δH ppm 1.45 (6H, 2×CH$_3$), 3.24 (4H, 2×CH$_2$), 3.43 (2H, CH$_2$), 3.87 (3H, CH$_3$) 4.55 (2H, OCH$_2$) 6.85 (4H), 7.3 (1H), 7.44 (2H), 7.67 (2H), 7.86 (2H).

m/z 477/479 M+H

Example 3(iii)

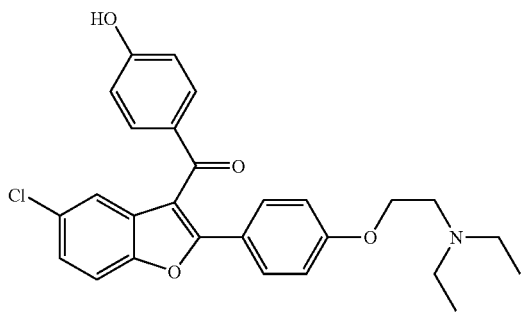

Pyridine hydrochloride (10 g) was heated to 170° C. Solid product from Example 3(ii) was added and the reaction was heated at 170° C. for a further 2 hours. The reaction was allowed to cool and ice-water added (100 mL) and the aqueous mixture was extracted using DCM (3×100 mL). The organic extracts were combined, dried (Na$_2$SO$_4$) and evaporated giving an oily residue. This was purified by flash chromatography (SiO$_2$) to give the title compound as a pale yellow foam (0.8 g, 63%)

$^1$H NMR (CDCl$_3$) δH ppm 0.91 (6H, 2×CH$_3$), 2.5 (4H, 2×CH$_2$), 2.75 (2H, CH$_2$), 4.03 (2H, OCH$_2$) 6.71 (2H), 6.88 (2H), 7.37 (4H), 7.69 (2H).

m/z 451/453 M+H

Example 3(iv)

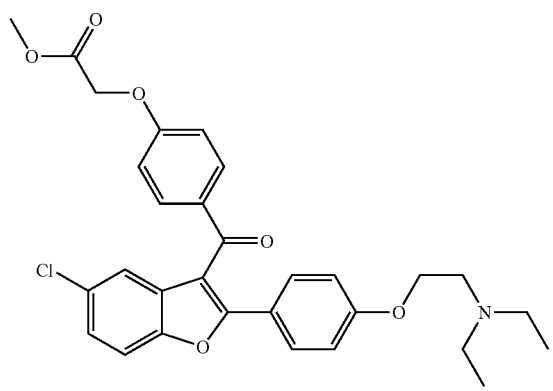

The title compound was prepared from the compound of Example 3(iii) using methods analogous to those described in Example 4(iv). 0.21 g 37% of product were obtained.

$^1$H NMR (CDCl$_3$) δH ppm 1.06 (6H, 2×CH$_3$), 2.62 (4H, 2×CH$_2$), 2.84 (2H, CH$_2$), 3.8 (3H, CH$_3$), 4.04 (2H, OCH$_2$) 4.6 (2H, OCH$_2$), 6.83 (4H), 7.29 (1H), 7.47 (2H), 7.61 (2H), 7.83 (2H).

Example 3(v)

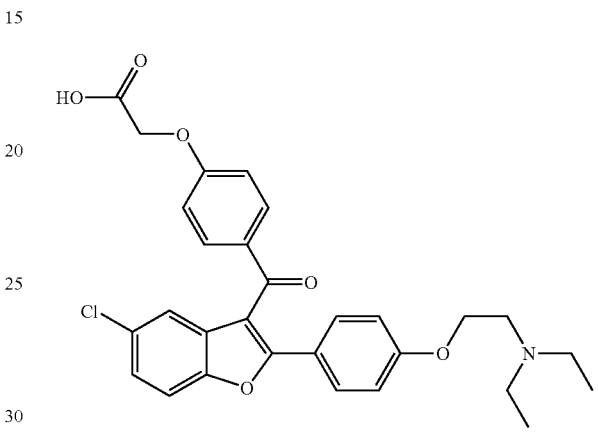

The title compound was prepared using methods analogous to those described in Example 1(vii).

$^1$H NMR (DMSO) δH ppm 1.14 (6H, 2×CH$_3$), 3.04 (4H), 3.3 (2H), 4.3 (2H, OCH$_2$), 4.6 (2H), 6.76 (2H), 6.90 (2H), 7.4 (3H), 7.6 (3H), 7.7 (1H).

m/z 522.28/524.47

Example 3(vi)

The compound of Example 3(v) was conjugated to a variety of chelates using methods analogous to those described in Example (viii)

Pn44 Conjugated (from Example 3(v))

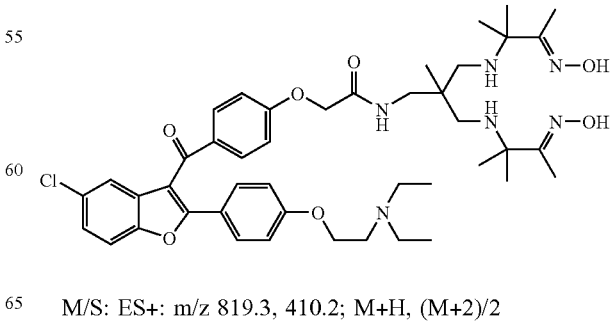

M/S: ES+: m/z 819.3, 410.2; M+H, (M+2)/2

Pn216 Conjugated (from Example 3(v))

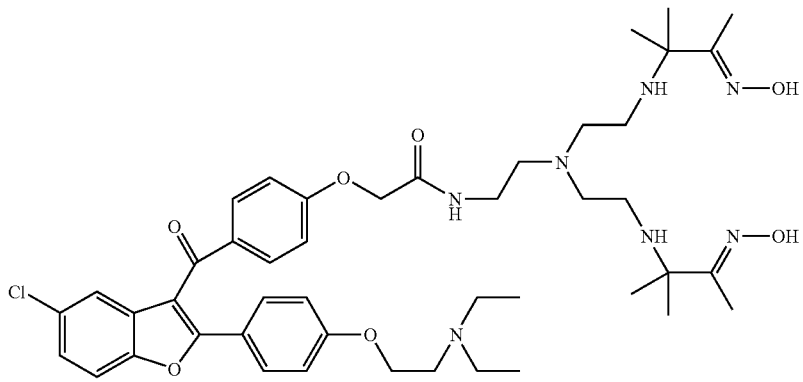

M/S: ES+: m/z 848.3, 424.7; M+H, (M+2)/2 cPn216 Conjugated (from Example 3(v))

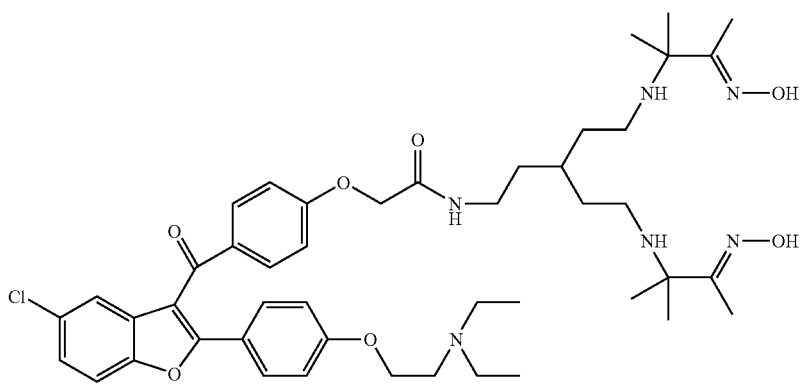

M/S: ES+: m/z 847.3, 424.5; M+H, (M+2)/2

Example 4

Example 4(i)

5-chloro-2-[4-(3-diethylaminopropyloxy)phenyl]benzofuran

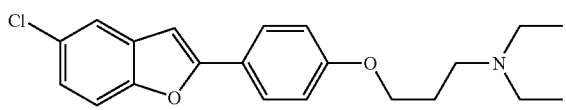

A solution of the Intermediate 1 (4 g, 16 mmol) in DMF was stirred at RT. Intermediate 2 (18 mmol) was added followed by potassium carbonate. The reaction was heated to 90° C. for 2 hours. The reaction was allowed to cool and was then poured onto ice-water. The resulting solid was collected by filtration and dried to give the title compound as a white solid 4.2 g, 76.4%).

$^1$H NMR (CDCl$_3$) δH ppm 1.04 (6H, 2×CH$_3$), 1.94 (2H, CH$_2$), 2.58 (6H, 3×CH$_2$), 4.07 (2H, OCH$_2$) 6.79 (1H), 6.95 (2H), 7.17 (1H), 7.38 (1H), 7.49 (1H), 7.74 (2H)

m/z 357/359 M+H

Example 4(ii)

5-chloro-2-[4(3-diethylaminopropyloxy)phenyl]-3-(4-methoxybenzoyl)benzofuran

A solution of the product from Example 4(i) (1 g, 2.8 mmol) in dry DCM was stirred at 0° C. under nitrogen. Anisoyl chloride (4.9 mmol) was added followed by a solution of SnCl$_4$ (1M DCM, 4.9 mmol). An immediate red colour occurred and stirring was continued for 2 hours. The reaction mixture was added carefully to 100 ml of ice-water and the aqueous was extracted with ethylacetate (3×100 Ml). The organic extracts were combined, dried (Na$_2$SO$_4$) and evaporated to give a bright yellow oil. This was purified by flash chromatography (silica flash) to give the title compound as a pale yellow solid. (0.8 g 58%).

$^1$H NMR (CDCl$_3$) δH ppm 1.42 (6H, 2×CH$_3$), 2.37 (2H, CH$_2$), 3.17 (6H, 3×CH$_2$), 3.89 (3H, CH$_3$)4.08 (2H, OCH$_2$) 6.82 (4H), 7.26 (1H), 7.45 (2H), 7.63 (2H), 7.84 (2H).

m/z 491/493 M+H

Example 4(iii)

5-chloro-2-[4-(3-diethylaminopropyloxy)phenyl]-3-(4-hydroxybenzoyl)benzofuran

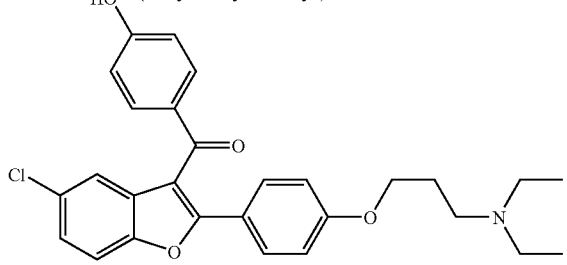

Pyridine hydrochloride (10 g) was heated to 170° C. Solid product from Example 4(ii) was added and the reaction was heated at 170° C. for a further 2 hours. The reaction was allowed to cool and ice-water added (100 mL) and the aqueous mixture was extracted using DCM (3×100 mL). The organic extracts were combined, dried (Na$_2$SO$_4$) and evaporated giving an oily residue. This was purified by flash chromatography (SiO$_2$) to give the title compound as a pale yellow solid (1.2 g, 61.4%)

$^1$H NMR (CDCl$_3$) δH ppm 1.11 (6H, 2×CH$_3$), 2.01 (2H, CH$_2$), 2.94 (4H, 2×CH$_2$), 3.31 (2H, CH$_2$) 4.08 (2H, OCH$_2$) 6.76 (2H), 6.96 (2H), 7.4 (2H), 7.56 (2H), 7.68 (2H), 7.75 (1H).

m/z 477/479 M+H

Example 4(iv)

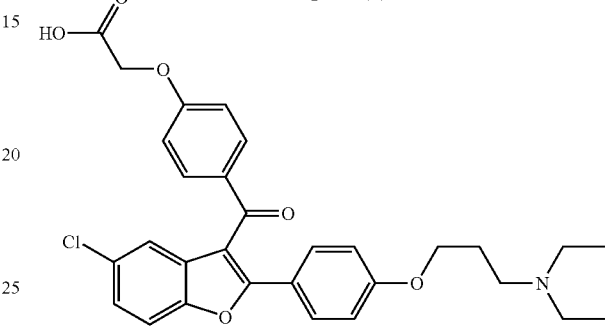

A solution of the product from Example 4(iii) (0.8 g, 1.8 mmol) in dry DMF was stirred at RT. Potassium carbonate was added and the reaction was heated to 90° C. for 2 hours. The reaction mixture was poured onto ice-water and the aqueous extracted using DCM (3×100 mL). The organic extracts were combined, dried (Na$_2$SO$_4$) and evaporated to give a yellow residue. This was purified using flash chromatography to give the title compound as an orange tar (0.13 g, 21%).

$^1$H NMR (CDCl$_3$) δH ppm 1.18 (6H, 2×CH$_3$), 2.22 (2H, CH$_2$), 2.79 (6H, 3×CH$_2$), 3.8 (3H, CH$_3$)4.08 (2H, OCH$_2$) 4.67 (2H, CH$_2$) 6.83 (4H), 7.27 (1H), 7.45 (2H), 7.65 (2H), 7.83 (2H).

m/z 549/551 M+H

Example 4(v)

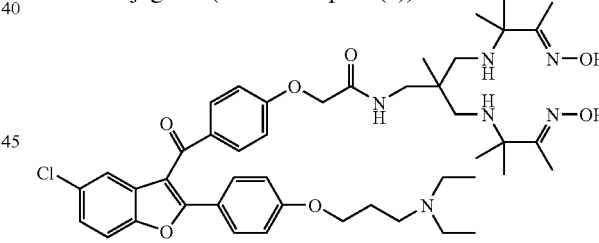

The title compound was prepared using methods analogous to those described in Example 1(vii).

$^1$H NMR (DMSO) δH ppm 1.26 (6H, 2×CH$_3$), 2.15 (2H), 3.22 (6H), 3.38 (2H), 4.16 (2H, OCH$_2$), 4.79 (2H), 6.9 (2H), 7.0 (2H), 7.5 (2H), 7.66 (2H), 7.84 (3H).

m/z 536.32/538.43

Example 4(vi)

The benzofuran of Example 4(v) was conjugated to a variety of chelates using methods analogous to those described in Example 1(viii)

Pn44 Conjugated (from Example 4(v))

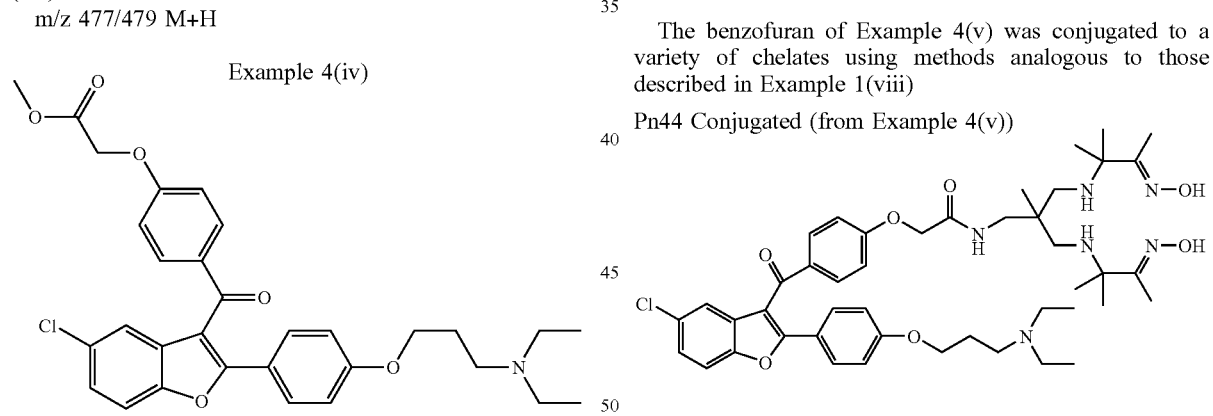

M/S: ES+: m/z 833.3, 417.6, M+H, (M+2)/2

Pn216 benzofuran3 Conjugated (from Example 4(v))

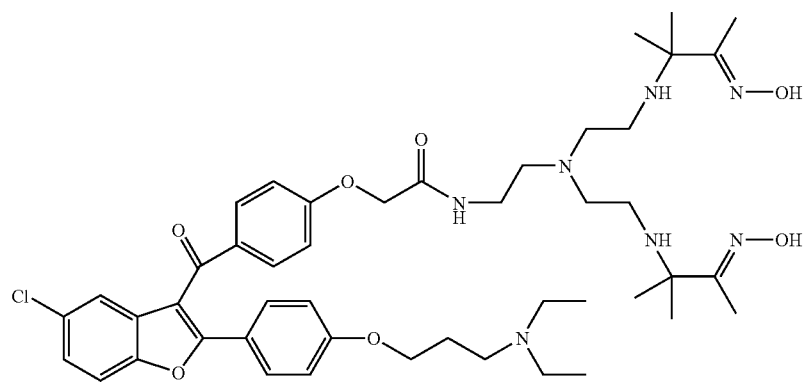

M/S: ES+: m/z 862.3, 432.1, M+H, (M+2)/2 cPn216 benzofuran3 Conjugated (from Example 4(v))

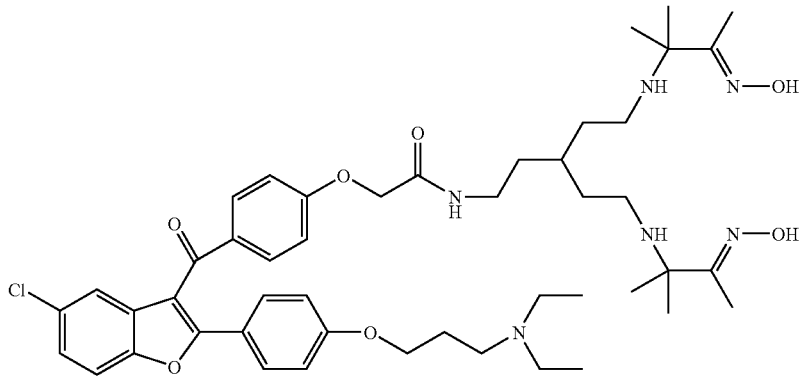

M/S: ES+: m/z 861.3, 431.4, M+H, (M+2)/2

Example 5

$^{99m}$Tc labelling of Compounds of the Invention (I)

A 0.1 ml aliquot of a 1 mg/ml solution of a compound of the invention dissolved in methanol or H$_2$O is transferred to a nitrogen-filled 10 ml glass vial together with deoxygenated saline (0.9% w/v, 1 ml) and 0.035 ml aqueous NaOH (0.1M). To this solution is added technetium generator eluate (1 ml, approx. 0.4 GBq) and then aqueous stannous chloride solution (0.1 ml, ca. 10 µg). The labelling pH is 9.0–10.0. Vials are incubated at ambient laboratory temperature (15–25° C.) for 30 minutes to effect labelling. HPLC purification is performed to remove unlabelled starting material and radioactive impurities prior to testing. After purification the organic solvent is removed under vacuum and the sample is redissolved in about 5 ml 0.1M phosphate buffer pH7.4 to give a working concentration of 6–9 MBq/ml. Radiochemical purity is assessed before use by the thin layer chromatography (TLC) system described below:

i) ITLC SG 2 cm×20 cm eluted with 0.9% w/v saline
ii) Whatman No.1 2 cm×20 cm eluted with 50:50 v/v acetonitrile:H$_2$O The labelled substrates remain at, or close to, the origin in TLC system (i) and move close to the solvent front in system (ii). When analysed by appropriate detection equipment the radiochemical purity is typically in excess of 85% labelled compound.

Example 6

$^{99m}$Tc Labelling of Compounds of the Invention (II)

A gluconate kit, comprising of sodium gluconate (1 mg) sodium bicarbonate (2 mg), stannous chloride (15 µg) is reconstituted with technetium generator eluate (5 ml, 2 GBq) and allowed to incubate at room temperature for 15 minutes to effect labelling. An aliquot (0.1 ml) of a compound of the invention freshly dissolved in methanol (5 mg/ml) is transferred to a nitrogen-filled 10 ml glass vial together with 0.025 ml aqueous NaOH (0.1M) and 2 ml of the $^{99m}$Tc-gluconate solution. The labelling pH is 9.0. Vials are incubated at room temperature for 30 minutes to effect labelling. Purification and assessment of radiochemical purity are carried out as for Example 5.

Example 7

$^{99m}$Tc Labelling of Compounds of the Invention (III)

A 0.1 ml aliquot of a compound of the invention dissolved in methanol (1 mg/ml) is transferred to nitrogen-filled 10 ml glass vial together with tricine dissolved in water (0.5 ml, 37.5 mg) and phosphinedynetris(benzene sulphonic acid)tris sodium salt dissolved in water (0.1 ml, 1 mg). To this solution is added technetium generator eluate (1 ml, approx 0.4 GBq) and then a solution of stannous chloride in 0.1M HCl (0.02 ml, ca 2 µg). The labelling pH is 4.5–5.5. Vials were incubated at 60° C. for 30 minutes to effect labelling. Purification and assessment of radiochemical purity is carried out as in Example 5.

Example 8

Preparation of 3-H Compounds

Example 8(i)

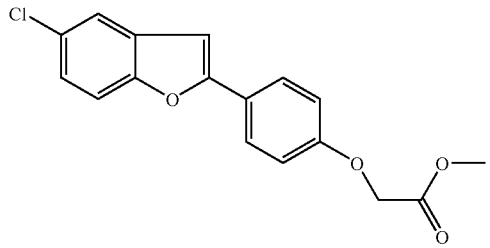

Intermediate 1 (200 mg, 8.17 10−4 mol), methylbromoacetate (0.38 mL, 4.09×10−3 mol, 5 eq) and potassium carbonate (1.129 g, 8.17×10−3 mol, 10 eq) were stirred in acetone (30 mL) and heated to reflux temperature. The mixture was refluxed for 5 hours. The reaction mixture was evaporated to dryness and the residue was partitioned between water and ethyl acetate. The layers were separated and the organic phase was washed with a further 2 portions of water. The organic phase was dried (Na2SO4) filtered and evaporated. The residue was purified by recrystallisation from ethyl acetate to afford the product as a white crystals (36)(125 mg, 48%)

$^1$H NMR (CDCl$_3$) δH ppm 3.83 (3H, OCH$_3$), 4.7 (2H, OCH$_2$) 6.84 (1H), 7.0 (d, 2H), 7.2 (d, $_1$H), 7.42 (d, $_1$H), 7.51 (d, 1H), 7.80 (d, 2H).

Example 8(ii)

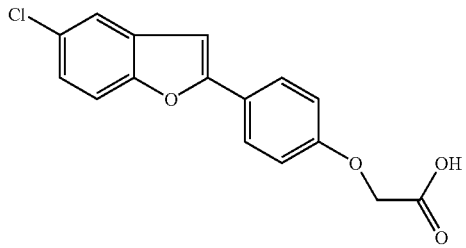

The title compound was prepared using methods analogous to those described in Example 1(vii).

Example 8(iii)

The following chelated compounds were prepared from the compound of Example 8(ii) using methods analogous to those described in Example 1(viii). When labelled with $^{99m}$Tc using the method described in Examples 5 to 7, these compounds may also be useful for imaging Alzheimer's disease and therefore represent a further aspect of the present invention.

Pn44 Conjugated

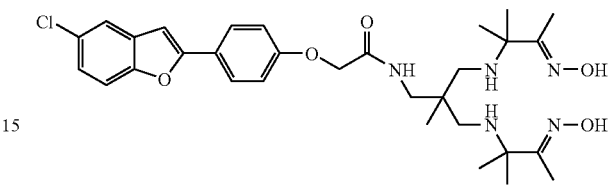

M/S: ES+: m/z: 600.2

1H NMR (DMSO): d 0.718 (s, 3H); 1.09 (s, 12H), 1.67 (s, 6H), 2.0 (m, 4H); 3.09 (m, 2H); 4.59 (s, 2H); 7.08 (d, 2H); 7.27 (s, 1H); 7.31 (m, 1H); 7.63 (d, 1H); 7.69 (m,$_1$H); 7.87 (d, 2H); 8.21 (bt, 1H); 10.36 (bs, 1H)

Pn216 Conjugated

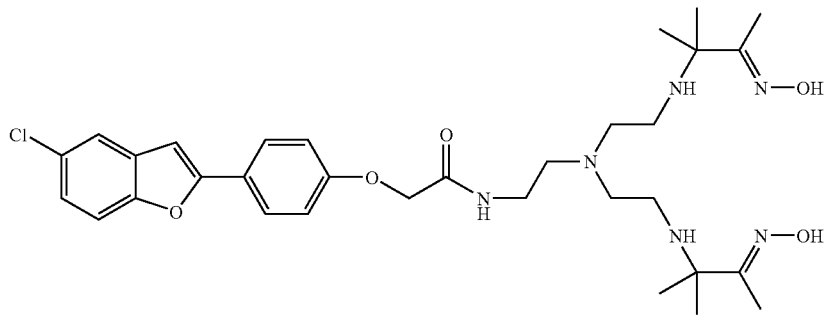

M/S: ES+: m/z: 629.2

1H NMR (DMSO): 1.010 (s, 12H), 1.69 (s, 6H), 2.26 (m, 4H); 2.42 (m, 2H); 3.18 (m, 2H); 4.85 (s, 2H); 7.08 (d, 2H); 7.26 (s, 1H); 7.30 (m, 1H); 7.63 (d, 1H); 7.67 (m, 1H); 7.87 (d, 2H); 8.01 (bt, 1H); 10.38 (bs, 1H)

cPn216 Conjugated

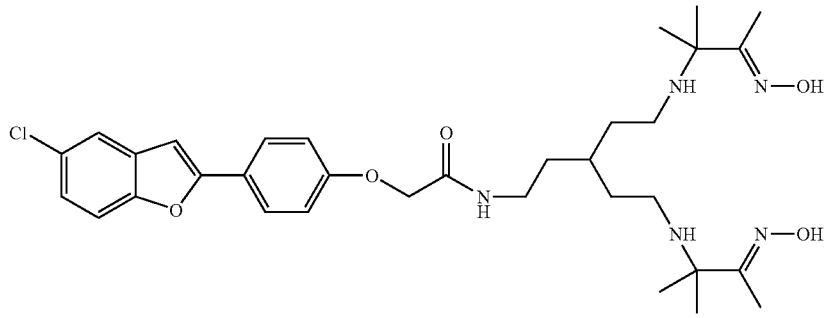

M/S: ES+: m/z 628.2 7.20 (s, 1H); 7.26 (dd, 1H); 7.54 (d, 1H); 7.61 (d, 1H); 7.80 (d, 2H); 8.12 (bt, 1H); 10.38 (bs, 1H)

DADP Conjugated

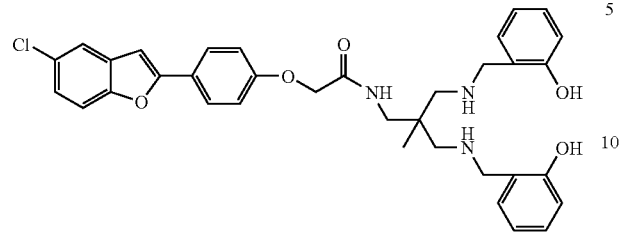

M/S: ES+: m/z 614.1

1H NMR: (DMSO): 0.79 (s, 3H), 2.33 (m, 4H); 3.11 (m, 2H); 3.70 (s, 4H); 4.61 (s, 2H); 4.86 (s, 1H); 6.70 (m, 4H); 7.05 (m, 6H); 7.27 (m, 2H); 7.62 (d, 1H); 7.68 (d, 1H); 7.90 (d, 2H); 8.20 (bt, 1H), 7.94 (s, 1H)

Biological Data

Determination of Amyloid Binding

The binding of Compounds was determined compared to the ability of $^{125}$I-beta amyloid protein 1-40 ($^{125}$I-BAP 1-40, Amersham Biosciences IM294)) to bind to amyloid 1-40 fibrils. Amyloid binding was essentially performed as follows.

Three fresh buffer stocks were prepared for experiments: Buffer 1, 50 mM HEPES/0.1% Bovine Serum Albumin (BSA) pH 7.5; Buffer 2, 50 mM HEPES/0.1% BSA/400 µM ZnCl$_2$ pH 7.5; Buffer 3, 50 mM HEPES/0.1% BSA/100 µM ZnCl$_2$ pH 7.5.

Streptavidin coated scintillation proximity assay beads (SA-SPA beads, Amersham Biosciences) were used to immobilise fibrillar Beta-Amyloid Protein (BAP 1-40). Amyloid coated beads (SPA-BAP) were prepared by incubating 250 µl SA-SPA beads (100 mg/ml) with 250 µl Buffer 2, 425 µl Buffer 1, 50 µl biotinylated BAP 1-40 (0.5 mg/ml, Biosource 03–243), 25 µl BAP 1-40 (10 mg/ml, Biosource 03–138). Non-specific binding SPA beads (SPA-NSB) were prepared to assess the binding of compounds to SPA beads with no associated BAP 1-40 fibrils in the following incubation: 250 µl SA-SPA beads (100 mg/ml) with 250 µl Buffer 2, 500 µl Buffer 1.

SPA-BAP and SPA-NSB incubations were left for 24 hours at room temperature and then spun 1.5 ml tubes (eppendorf, Merk, 306/0421/12) for 2 minutes at 1000×g. The supernatants were removed and the beads were washed twice by resuspending them in 1 ml Buffer 3 followed by centrifugation for 2 minutes at 1000×g. Finally, washed SPA-BAP and SPA-NSB beads were resuspended in 1 ml Buffer 3.

Amyloid binding of $^{125}$I-BAP 1-40 and test compounds was performed in triplicate in 0.5 ml tubes (eppendorf, Merk, 306/0421/02) by adding 50 µl SPA-BAP beads to 25 µl Buffer 2 and 25 µl labelled compound ($^{125}$I-BAP 1-40 or test compound). Tubes were then incubated for 180 minutes at room temperature with shaking, followed by centrifugation for 2 minutes at 1000×g. The supernatants were removed and SPA-BAP pellet washed twice with 300 µl Buffer 3 containing 1% TWEEN-20 (Sigma, P7949). Non-specific binding for labelled compounds to the SPA beads was determined using incubations as described above but by substituting SPA-BAP beads with SPA-NSB beads. Radioactivity associated with the washed SPA bead pellets was then determined.

The affinity of labelled compounds for fibrillar BAP 1-40 was estimated by subtracting SPA-NSB associated counts from SPA-BAP associated counts. The binding of labelled compounds was then compared to $^{125}$I-BAP binding, which was taken as being 100%.

In these experiments, $^{125}$I-BAP 1-40 or test compounds were added in equimolar amounts.

RESULTS AND DISCUSSION

BAP 1-40 readily self-aggregates. In this assay, the binding of $^{125}$I-BAP 1-40 to a fixed amount of amyloid fibrils immobilised on SPA beads was used as a reference for other compounds. Table 1 shows how other amyloid binders and non-binders compare to the binding of $^{125}$I-BAP 1-40. The test compounds bind to amyloid fibrils with 40, 15 and 23% the affinity of $^{125}$I-BAP 1-40 respectively, which is favourable compared to the $^{125}$I-labelled BAP 15–21 sequence (Amersham Biosciences) (21%) and the $^{99m}$Tc-labelled BAP 15–21 sequence (9%). The BAP 15–21 sequence is responsible for the binding of BAP to itself during the formation of amyloid fibrils.

TABLE 1

| Compound | Amyloid binding (% of 125I-BAP 1-40) |
| --- | --- |
| $^{125}$I-BAP 1-40 | 100 |
| Compound of Example 8(iii) Pn216 conjugated | 40 |
| Compound of Example 2(vii) Pn216 conjugated | 15 |
| Compound of example 1(vii) Pn216 conjugated | 23 |
| $^{125}$I-KKLVFFA (BAP 15-21) | 21 |
| $^{99m}$Tc-Pn216-KKLVFF (BAP 15-20) | 9 |

The invention claimed is:
1. A compound of formula (I):

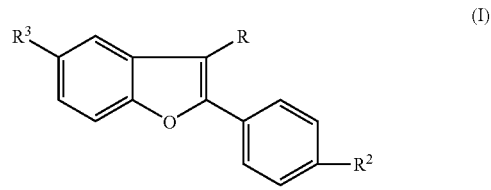

or a salt thereof, wherein either:
(i) R is hydrogen and R$^2$ is the group —OCR$^4$R$^5$[B]-[A] wherein R$^4$ and R$^5$ are independently selected from hydrogen and C$_{1-6}$ alkyl, [A] is a chelate, and [B] is a linking group and is preferably —C(O)NR$^6$— wherein R$^6$ is hydrogen or C$_{1-6}$ alkyl; or
(ii) R is the group

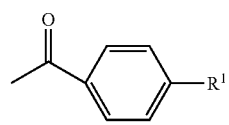

and one of R$^1$ and R$^2$ is the group —OCR$^4$R$^5$[B]-[A] as defined above; and
the other is the group —(O)$_n$—C$_{1-6}$ alkyl-NR$^7$R$^8$ wherein n is 0 or 1, and R$^7$ and R$^8$ are independently selected from hydrogen and C$_{1-6}$ alkyl; and
R$^3$ is halo, preferably chloro.

2. A compound according to claim 1 of formula (Ia):

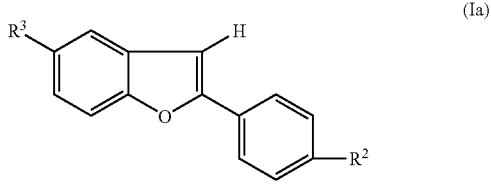

(Ia)

or a salt thereof, wherein $R^2$ is the group —$OCR^4R^5$[B]-[A] wherein $R^4$ and $R^5$ are independently selected from hydrogen and $C_{1-6}$ alkyl, [A] is a chelate, and [B] is a linking group and is preferably —$C(O)NR^6$— wherein $R^6$ is hydrogen or $C_{1-6}$ alkyl;

and $R^3$ is halo, preferably chloro.

3. A compound according to claim 1 of formula (Ib):

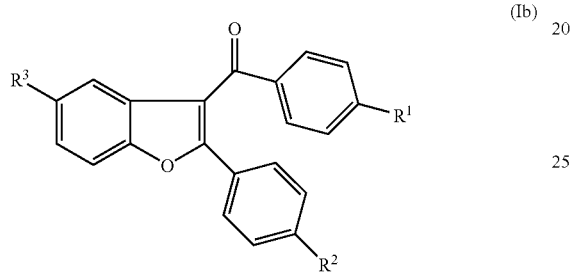

(Ib)

or a salt thereof, wherein:
one of $R^1$ and $R^2$ is the group —$OCR^4R^5$[B]-[A] as defined in claim 1; and
the other is the group —$(O)_n$—$C_{1-6}$ alkyl-$NR^7R^8$ as defined in claim 1; and
$R^3$ is halo, preferably chloro.

4. A compound according to claim 3 of formula (Ic):

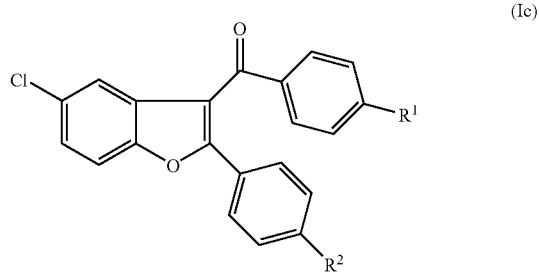

(Ic)

or a salt thereof, wherein:

one of $R^1$ and $R^2$ is —$OCH_2C(O)NH$-[A] wherein [A] is a chelate;
the other is —O—$(CH_2)_{2,3}$—$NR^7R^8$ wherein $R^7$ and $R^8$ are independently selected from hydrogen and $C_{1-6}$ alkyl.

5. A compound of formula (II)

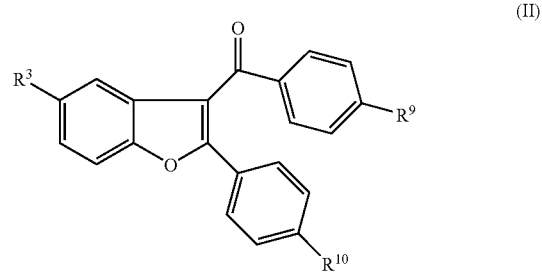

(II)

or a protected derivative thereof, wherein one of $R^9$ and $R^{10}$ is —$OCR^4R^5C(O)OH$ wherein $R^4$ and $R^5$ are independently selected from hydrogen and $C_{1-6}$ alkyl; and the other is —$(O)_n$—$C_{1-6}$ alkyl-$NR^7R^8$ wherein n is 0 or 1, and $R^7$ and $R^8$ are independently selected from hydrogen and $C_{1-6}$ alkyl; and R3 is halo, preferably chloro.

6. A radiolabelled compound selected from compounds of formula (I), (Ia), (Ib), or (Ic) according to any one of claims 1 to 4, labelled with $^{99m}$Tc.

7. A radiopharmaceutical formulation comprising the compound of claim 6 and one or more pharmaceutically acceptable excipients.

8. A kit for the preparation of a radiopharmaceutical comprising a compound of formula (I), (Ia), (Ib), or (Ic) according to any one of claims 1 to 4 and instructions for making the radiopharmaceutical.

9. A method for in vivo imaging or diagnosis of Alzheimer's disease, familial Alzheimer's disease, type II diabetes, Down's syndrome, homozygotes for the apolipoprotein E4 allele, rheumatoid arthritis, systemic amyloidosis (primary and secondary), and haemorrhagic stroke which comprises administration of a radiopharmaceutical formulation according to claim 7 in an amount of 0.1 to 50 mCi and then recording an image using SPECT Imaging.

* * * * *